US006589254B2

(12) United States Patent
Fontenot

(10) Patent No.: US 6,589,254 B2
(45) Date of Patent: Jul. 8, 2003

(54) BREAST BRACKET

(76) Inventor: Mark G. Fontenot, 229 Marilyn Dr., Lafayette, LA (US) 70503

( * ) Notice: Subject to any disclaimer, the term of this patent is extended or adjusted under 35 U.S.C. 154(b) by 0 days.

(21) Appl. No.: 10/099,309

(22) Filed: Mar. 12, 2002

(65) Prior Publication Data
US 2002/0099264 A1 Jul. 25, 2002

Related U.S. Application Data

(63) Continuation of application No. PCT/US00/25141, filed on Sep. 13, 2000.
(60) Provisional application No. 60/153,767, filed on Sep. 14, 1999.

(51) Int. Cl.[7] ............................................. A61B 19/00
(52) U.S. Cl. ........................ 606/130; 600/231; 600/235
(58) Field of Search ...................... 606/130; 600/231, 600/208, 232, 233, 235

(56) References Cited

U.S. PATENT DOCUMENTS

| | | |
|---|---|---|
| 2,493,598 A | 1/1950 | Rozek |
| 3,394,700 A | 7/1968 | Yamamoto |
| 4,099,521 A | 7/1978 | Nestopr et al. |
| 4,355,631 A | 10/1982 | LeVahn |
| 5,056,523 A | 10/1991 | Hotchkiss, Jr. et al. |
| 5,109,831 A | 5/1992 | Forrest et al. |
| 5,201,742 A | 4/1993 | Hasson |
| 5,207,688 A | 5/1993 | Carol |
| 5,423,832 A | 6/1995 | Gildenberg |
| 5,437,280 A | 8/1995 | Hussman |
| 5,499,989 A | 3/1996 | LaBash |
| 5,545,123 A | 8/1996 | Ortiz et al. |
| 5,678,549 A | 10/1997 | Heywang-Koebrunner et al. |
| 5,702,405 A | 12/1997 | Heywang-Koebrunner et al. |
| 5,706,811 A | 1/1998 | Takeda et al. |
| 5,772,654 A | 6/1998 | Leyva |
| 5,795,308 A | 8/1998 | Russin |
| 5,807,276 A | 9/1998 | Russin |
| 5,879,291 A | 3/1999 | Kolata et al. |
| 5,913,863 A | 6/1999 | Fischer et al. |
| 5,921,979 A * | 7/1999 | Kovac et al. .................. 606/1 |
| 5,938,592 A | 8/1999 | Koteles et al. |
| 6,019,722 A * | 2/2000 | Spence et al. .............. 600/235 |
| 6,022,362 A | 2/2000 | Lee et al. |
| 6,080,114 A | 6/2000 | Russin |

* cited by examiner

*Primary Examiner*—Paul J. Hirsch
(74) *Attorney, Agent, or Firm*—Townsend and Townsend and Crew LLP

(57) ABSTRACT

Methods and systems for stability of a human breast during biopsy and surgical procedures are disclosed. An outward lesion is applied to external surface regions of the breast to facilitate and increase the accuracy of access to lesions and other target sites.

11 Claims, 12 Drawing Sheets

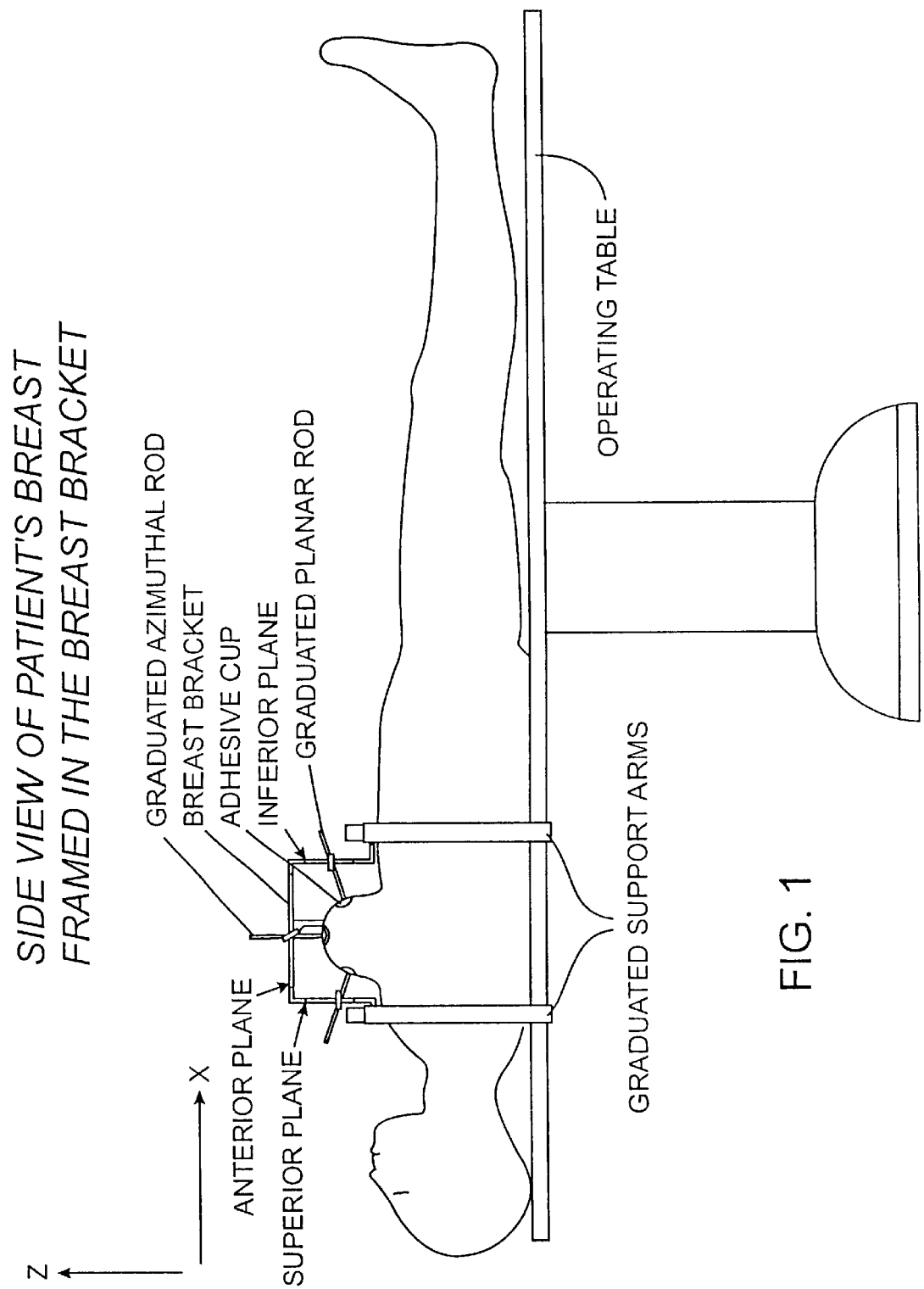

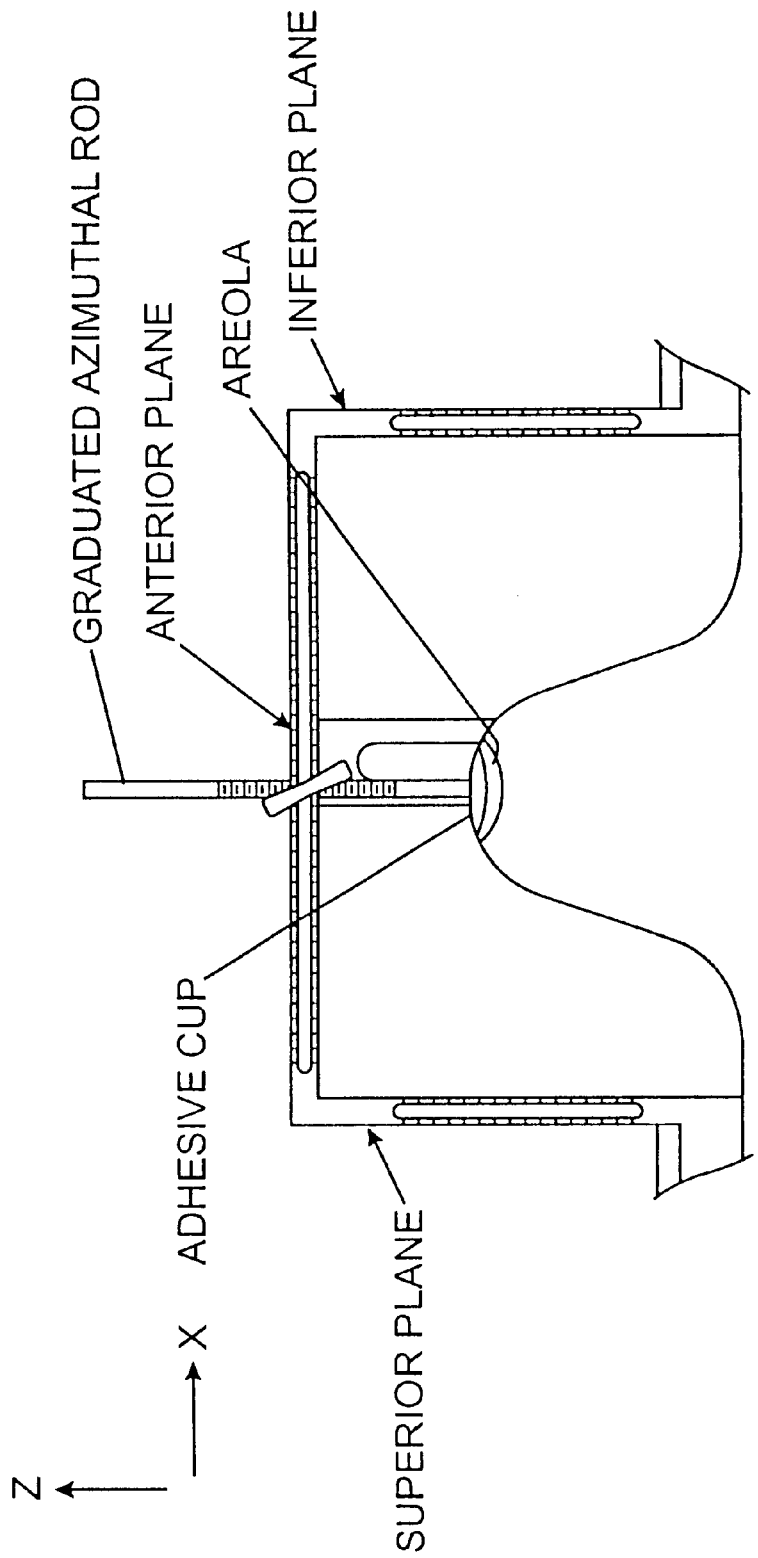

*TOP VIEW OF ANTERIOR PLANE TENTED BREAST FRAMED IN THE BREAST BRACKET*

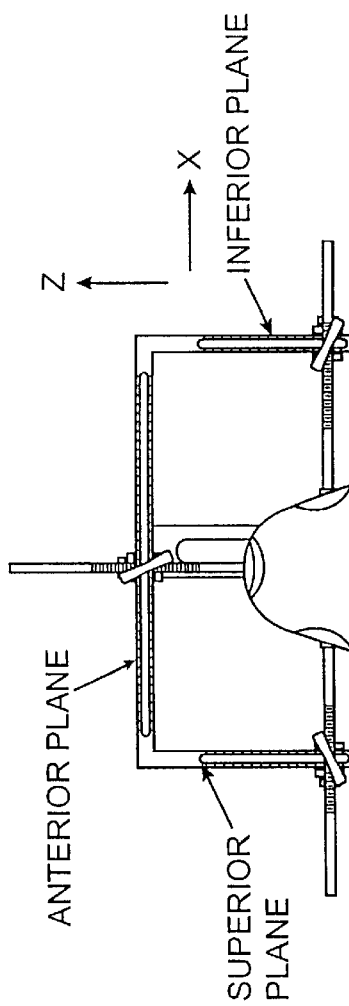
FIG. 4A
FIG. 4C
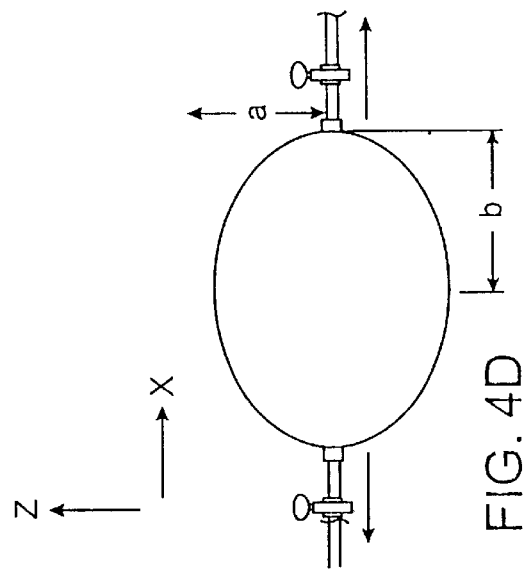
FIG. 4B
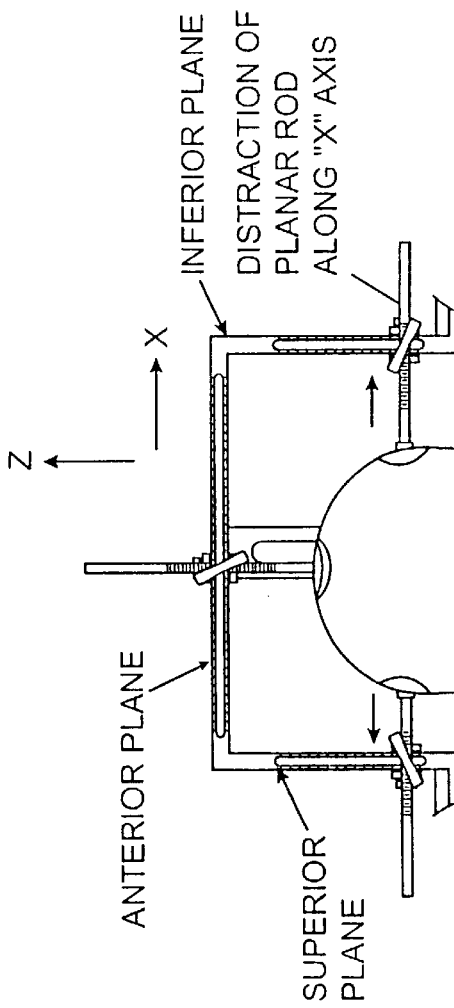
FIG. 4D

RADIOGRAPHY USING THE BREAST BRACKET - BREAST IN NEUTRAL POSITION

RADIOGRAPHY USING THE BREAST BRACKET - COMPRESSED BREAST

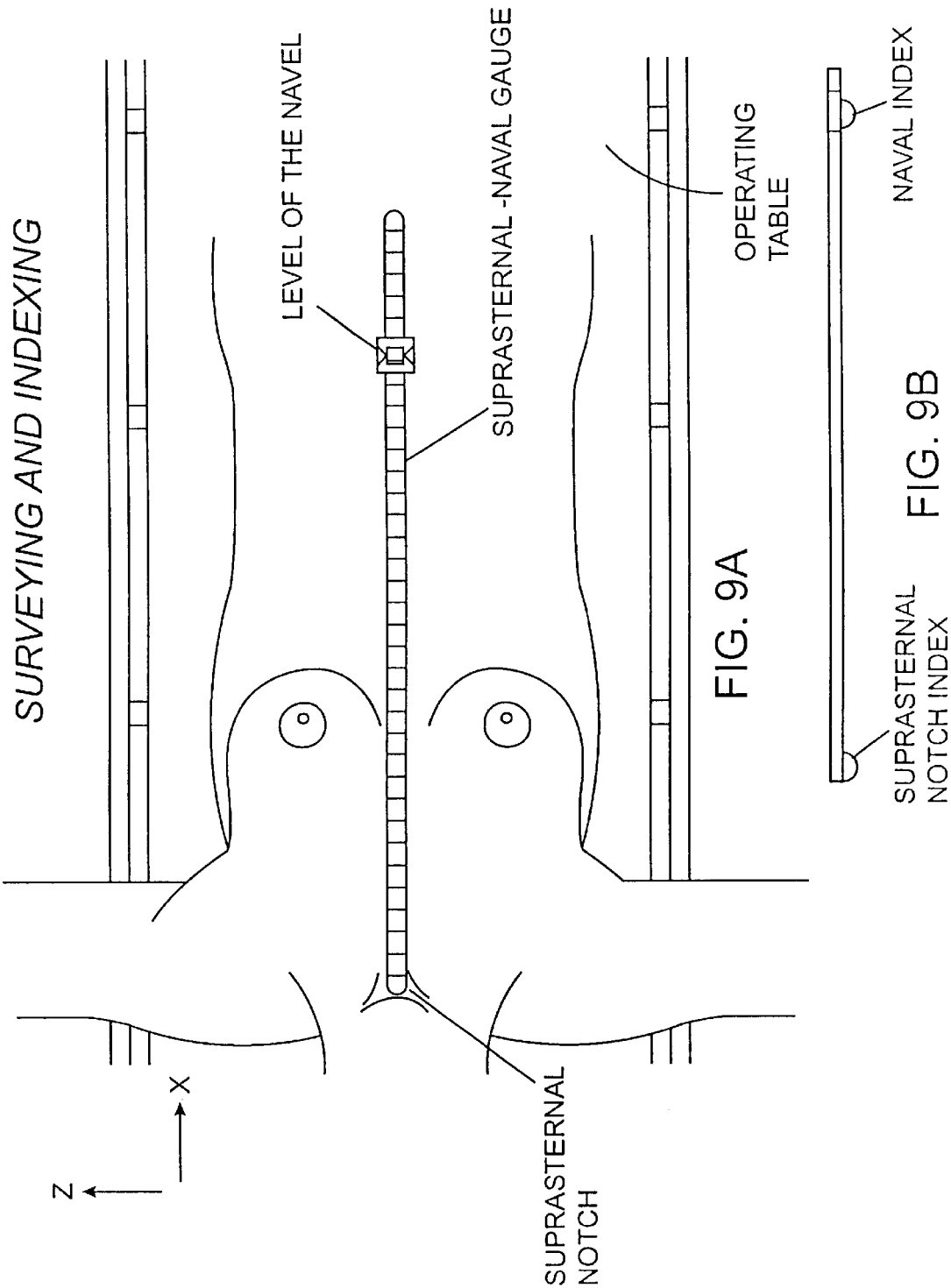

BREAST BRACKET

CROSS-REFERENCES TO RELATED APPLICATIONS

This application is a continuation of PCT/US00/25141 (Attorney Docket No. 019970-000110PC), filed on Sep. 13, 2000, which claimed the benefit of provisional application No. 60/153,767 (Attorney Docket No. 019970-000100), filed on Sep. 14, 1999, the full disclosures of which are incorporated herein by reference.

BACKGROUND OF THE INVENTION

The present invention relates to methods and devices which retain and position a breast in a graduated reference frame while the patient in either in the supine or prone position for the purposes of instrumenting the breast for various procedures and techniques including but not limited to surgery, biopsy, tissue retraction, deployment of devices, radiography, imaging, spatial positioning, and repeatability.

BRIEF SUMMARY OF THE INVENTION

1. Objects of the Invention

It is an object of the invention to provide a method and device that will support the breast in a position that enhances surgical and biopsy procedures using a variety of devices, methods, and techniques.

It is another object of the invention to provide efficient stabilization and traction of the breast as well as provide a means for retraction of tissue during surgical procedures of the breast.

It is still another object of the invention to provide support, guidance, and deployment of surgical instruments and devices during surgical and biopsy procedures of the breast.

It is still yet another object of the invention to provide a method and device to repeatedly position the breast in a reference frame for the purposes of survey the breast for a biopsy or surgical procedure or repeatedly position the breast for diagnostic radiography or therapeutic radiation.

It is an object of the invention to provide a reference frame encompassing the breast and when used in combination with imaging and processing techniques such as CT or MRI, the surgeon can precisely locate a lesion relative to the reference frame.

It is another object of the invention to provide support for the breast during radiographic techniques such as mammography while the patient is lying on their back or in the supine position.

In yet another objective, the invention provide an operative platform for a variety of excisional and surgical devices to be used in a more accurate and repeatable manner.

2. Summary of the Invention

Recently, several patents surrounding the use of devices for minimally invasive breast biopsy or the excision of breast tissue have been issued. For example, Lee and Vetter in U.S. Pat. No. 6,022,362 disclose an excisional biopsy device consisting of a tubular member with a bowed cutting edge at the distal aspect of the device. After placing the device adjacent to a suspected lesion in the breast, the bowed cutting tool is deployed and the device is manually rotated which excises tissues for removal. In particular, the instrument is supported and deployed manually. The present disclosure describes methods and devices that would allow the Lee and Vitter device to be integrated into the present invention resulting in improved operation of their patent.

In another example, Russin in U.S. Pat. Nos. 5,795,308; 5,807,276; and 6,080,114 describe a biopsy device and method wherein a rigid K-wire is positioned through a breast lesion to be removed under radiographic guidance. An introducer tube is advanced over the rigid K-wire and placed into position and the K-wire is removed. Next, a rigid rod with flexible steel hooks is advanced through the tube, exits the distal aspect of the tube and engages the breast tissue. The tube is withdrawn and series of instruments are passed over the anchored rigid rod resulting in the removal breast tissue using a cannula. To retain and position the breast, a stabilizing tong is disclosed such that the breast is compressed along the axis of the rod to foreshorten the distance from skin to breast lesion. Compression of the breast along the axis of the rod results in radial expansion of the breast tissue including the lesion the lesion to be removed (Poisson effect). This may result in an excisional biopsy that either leaves some of the lesion remaining in the breast as a result of a larger lesion in a plane perpendicular to the long axis of the rod, or compel the operator to use a larger cannula to capture all of the radially expanded lesion. The present invention disclosed herein, describes a device that would allow Russin to practice his invention in a more efficient and precise manner.

Wire needle localization is a surgical technique frequently invoked by surgeons to biopsy lesions in the breast. A wire is inserted adjacent to a breast lesion under the guidance of radiography. The wire serves as a marker which is palpated by the surgeon at the time of and during surgery in order to estimate the dissection route to remove the breast tissue to be biopsied as well as guide to estimate the thickness of the margin during the procedure. The surgical objective of the biopsy is to remove an adequate tissue sample such that the wire and the lesion are at the center of the sample surrounded by an adequate margin thickness of normal breast tissue. About 20% of wire needle localizations submitted for pathologic evaluation are returned as malignant. Of these, many have dirty margins meaning that some of the malignant was left in the breast compelling the surgeon to return to the operative site in the breast and remove additional tissue that is suspect of the malignant tumor.

Surgery and biopsy of the breast using the aforementioned methods and devices is typically performed with the patient lying on their back. In this position, the breast will lay somewhat off center and lateral to the patient's chest, the amount of which is dependent primarily on the size of the breast as well as the age of the patient. Managing the breast during surgical procedures can be time consuming and inefficient. Stabilization of the breast using the present invention will result in more efficient and accurate of devices and methods for biopsy and surgical procedures.

BRIEF DESCRIPTION OF THE DRAWINGS

FIG. 1 is a schematic side view in the x-z plane of a female in the supine position on an operating table with the breast framed in the breast bracket. The breast bracket is retained and reversibly coupled to the operating table. The adhesive cups are reversibly attached to all graduated rods (azimuthal and planar). The breast is framed in the bracket using adhesive cups which are reversibly adhered to the skin and nipple. Tenting of the breast is facilitated when the rods with the adhesive cups are attached to the breast and distracted resulting in distention of the skin and breast tissue, thus expanding the space that the breast occupies within the breast bracket.

FIG. 4 are side views of the breast framed in the breast bracket. FIGS. 4(a) and 4(b) shows a breast in the relaxed position. Specifically, FIG. 4(a) shows the azimuthal rod displacing the breast in generally the anterior or z direction and the FIG. 4(b) shows the cross section of the breast in the x-y plane as a result of distracting the breast generally in the anterior or z direction. In FIGS. 4(c) and 4(d), the planar rods are oppositely displaced along the x axis resulting in the expansion of the breast along the x-axis simultaneous to a contraction of breast tissue along the z-axis (FIG. 4(d)).

FIG. 7 are side and top views of a breast framed in the breast bracket undergoing radiography.

FIG. 8 are side and top views of a breast framed in the breast bracket undergoing radiography. The moveable superior and inferior compression plates are displaced toward one another along the x axis causing compression of the breast.

FIG. 9 are top and side views of the graduated suprasternal-naval gauge. FIG. 9(a) shows a top view of anterior aspect of the graduated suprasternal-naval gauge reversibly placed in the suprasternal notch and the sliding naval index placed in the naval. After placement of the suprasternal and naval indexes in the suprasternal notch and naval, respectively, the distance from the naval to the suprasternal notch can be read and recorded at the level of the naval. FIG. 9(b) is a side view of the graduated suprasternal-naval gauge showing the hemispherical suprasternal and naval indexes.

DETAILED DESCRIPTION OF THE INVENTION

Referring to FIGS. 1 and 2, these schematics depict a breast framed in the breast bracket in the x-z plane of a patient in the supine position on an operating table. Procedurally, the patient is first placed in the supine position on an operating table. The graduated support arms of the breast bracket are reversibly and moveably coupled to the lateral aspects of the operating table. The breast bracket is reversibly coupled to the graduated support arms and positioned over the desired breast. The graduated azimuthal rod and adhesive cup are assembled and placed in the rod guide of the rod holder on the anterior plane of the breast bracket. The azimuthal rod-adhesive cup-rod holder assembly is reversibly and moveably attached to the anterior plane of the breast bracket. Specifically, the rod holder can be moveably positioned and fixed at any point within the boundaries of the anterior plane of the breast bracket (FIGS. 1 and 2) The azimuthal rod can be advanced or retracted and fixed at a desired position while in the rod guide (FIG. 2(a)).

Once the azimuthal rod-adhesive cup assembly is fitted into the anterior plane rod holder of the breast bracket, the nipple is then positioned in the center of the adhesive cup. The adhesive nipple-areola cup is indexed to the nipple such that the nipple is positioned in the center of the adhesive cup of the azimuthal rod. After securing the azimuthal rod-adhesive cup assembly to the nipple, the rod is distracted so as the expand or stretch the breast generally in the anterior or z direction or in a final desired position (FIG. 2(a)). The desired position of the azimuthal rod can be fixed and recorded by reading the final (x,y) position of the graduated frame in the anterior plane of the breast bracket. The distraction point can be recorded from the graduated azimuthal rod relative to the rod guide (FIGS. 3(a) and 3(b)).

Figure 2B:
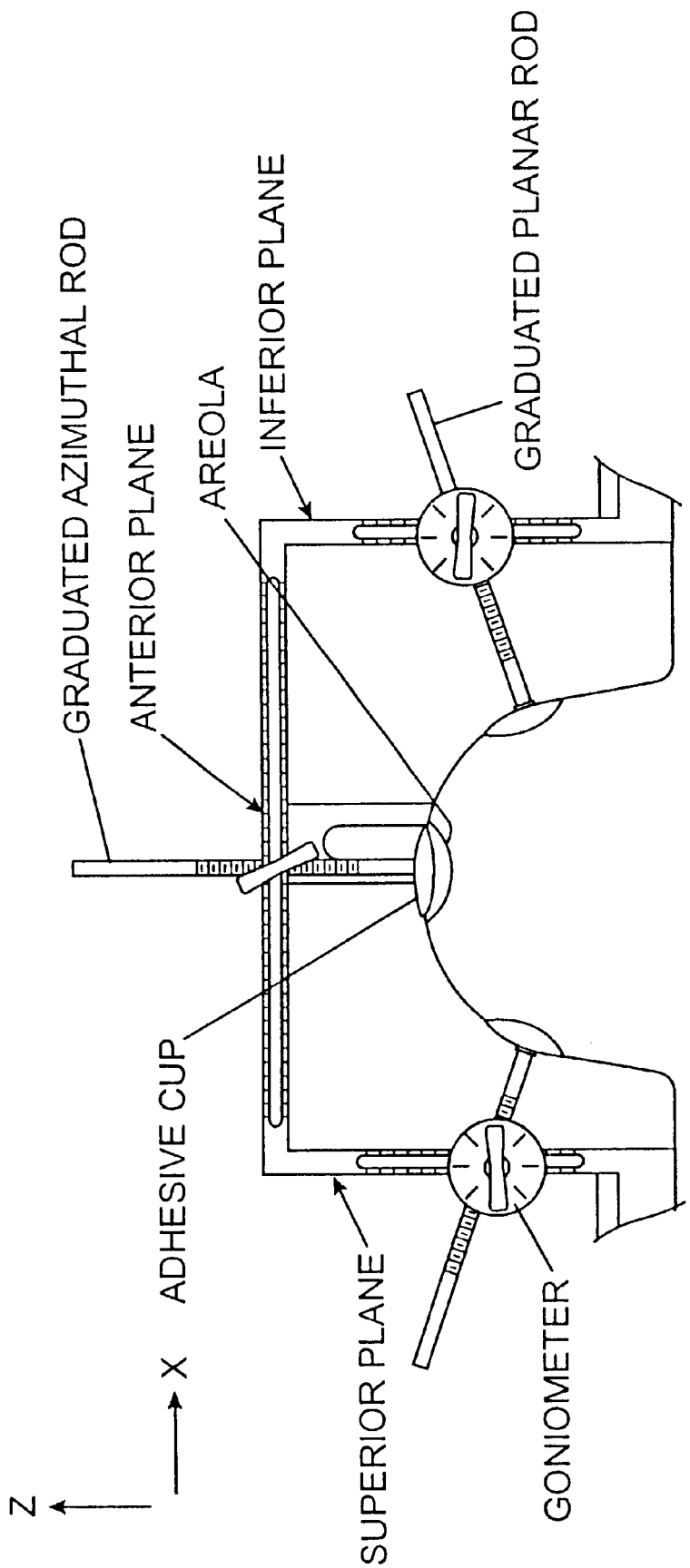
FIG. 2 is a side view in the x-z plane of a breast framed in the breast bracket. After positioning the frame over the breast using the frame, the graduated azimuthal rod with the adhesive cup is fixed over the nipple and all or part of the areola (FIG. 2(a)). The nipple is positioned in the center of the adhesive cup. The adhesive nipple-areola cup is indexed to the nipple such that the nipple is in the center of the adhesive cup. Once the azimuthal rod is secured to the nipple, the rod is retracted anteriorly or in the z direction so as the distend or stretch the breast to the desired position. Then, the planar rods-adhesive cup assemblies are attached to the skin of the breast and distracted away from the breast causing the breast to expand or be distended (FIG. 2(b)).
FIG. 2(c) shows a top view of the superior plane of the breast bracket with the planar rod holder reversibly and moveably attached to the graduated superior-anterior and superior-posterior frames.

In FIG. 2(b), the planar rods are assembled with the adhesive cups and placed in the rod guides that are housed by the superior, inferior, medial, and/or lateral plane rod holders of the breast bracket. From FIG. 2(b), the adhesive cup of the planar rod assembly fitted into the rod guide (FIG. 2(c)) of the rod holder. The adhesive cup is attached to the skin of the breast. The planar rod assembly attached to the skin of the breast is distracted into the final desired position. In one embodiment from FIG. 2(b), the two planar rod guides (FIG. 2(c)) of the rod holders allow the planar rods to rotate in the x-z plane. The desired amount of rotation can be recorded in degrees from a goniometer attached to the rod guides.

Figure 2C:
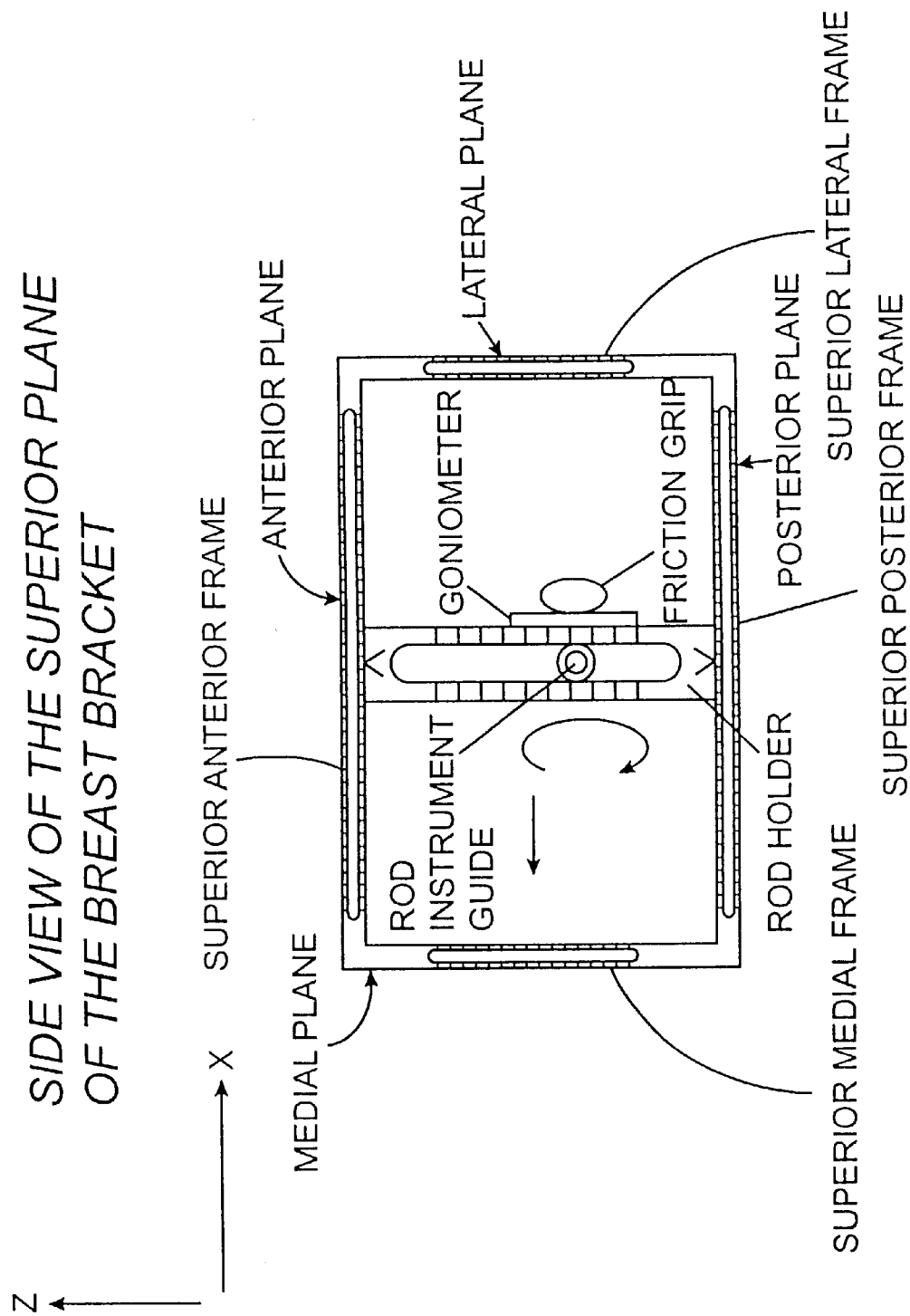

FIG. 2(c) shows a top view of the superior plane of the breast bracket with the rod holder reversibly and moveably attached to the graduated superior-anterior and superior-posterior frames. The rod holder can be moved along the y axis and fixed at the desired position. The rod guide is reversibly and moveably attached to the rod holder. The rod guide can be moved along the z axis as well as rotate in the x-z plane.

The rod holder in FIG. 2(c) can be rotated 90 and reversibly and moveably attached to the graduated superior-medial and superior-lateral frames. The rod holder can be moved along the z axis and fixed at a desired position. The rod guide is reversibly and moveably attached to the rod holder. The rod guide can be moved along the y axis as well as rotate in the x-y plane.

Figure 3A:
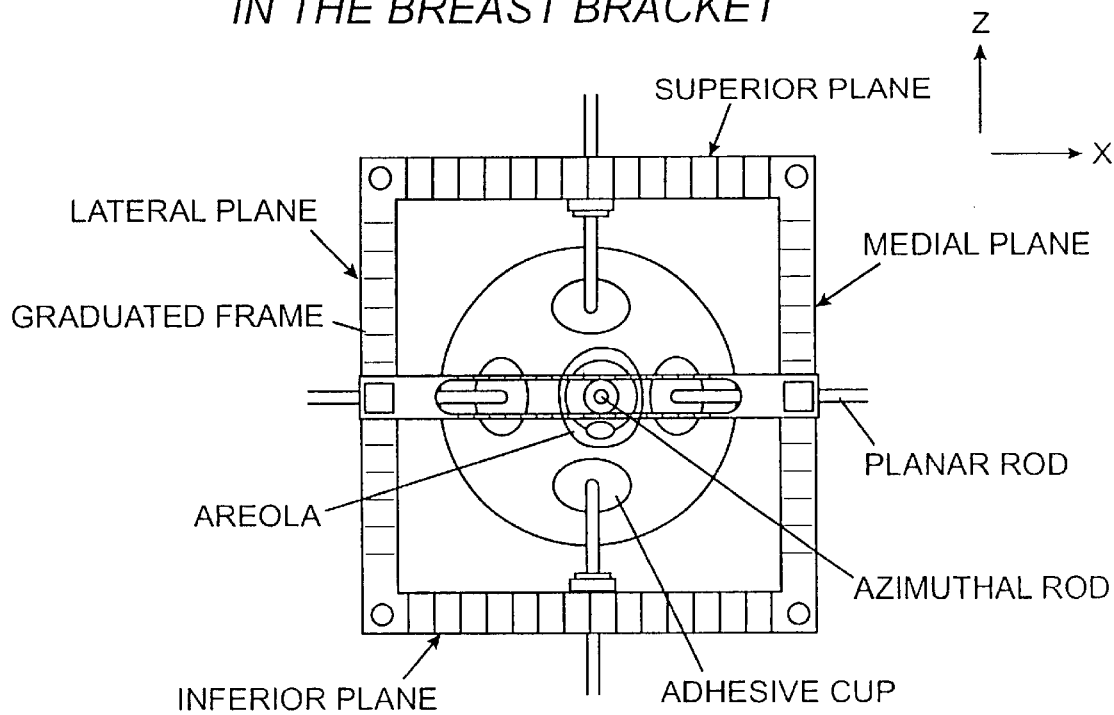
FIG. 3 are top views of a breast framed in the breast bracket using a pentarod (a) or quadrarod (b) configuration. In the pentarod configuration (FIG. 3(a)), four planar rods and an azimuthal rod are used to expand and tent the breast. In the quadrarod configuration, three planar rods and an azimuthal rod are used to expand and tent the breast.
Figure 3B:
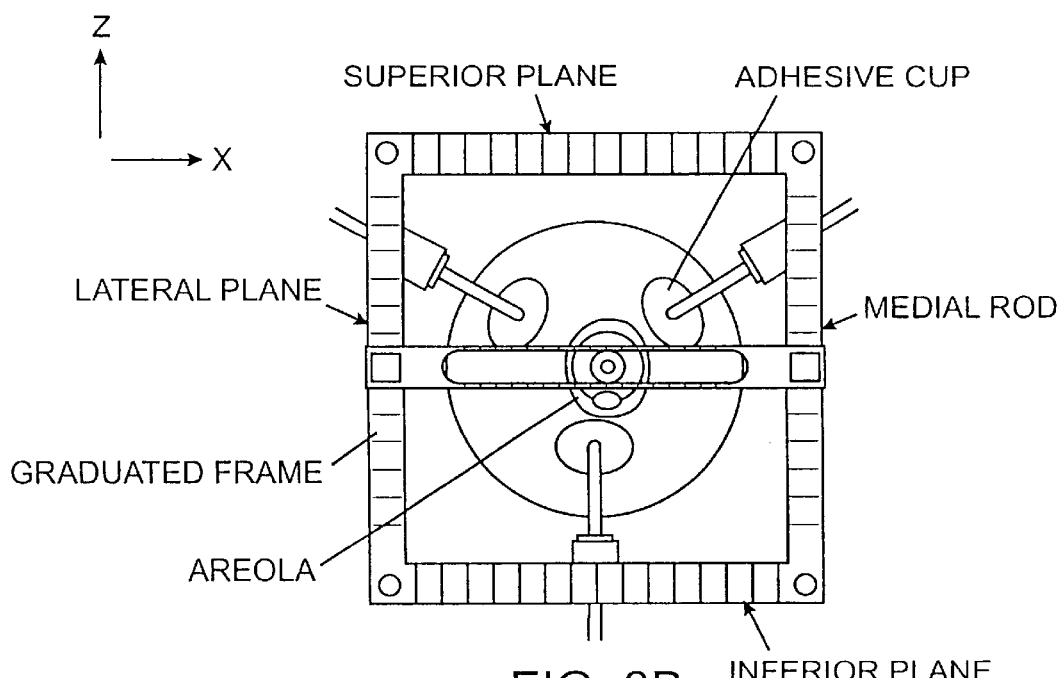

From FIGS. 2(b), 3(a), and 3(b), the planar rod-adhesive cup assembly can be positioned anywhere within the boundaries of the breast bracket on either the superior, inferior, lateral, and medial plane. Depending on the type of planar rod holder used to couple the planar rod to the breast bracket in the respective plane, the x, y and z position can be recorded as well as the rotation of the planar rod in the x-y, y-z, and x-z plane. Take, for example, the planar rod assembly shown in FIG. 3(b). The medial plane is considered the y-z plane and as such both ends of the planar rod holder are positioned to the anterior-medial frame at coordinate point (y,z) and the postior-medial frame at coordinate point (y,z). The position of the planar rod guide is by the coordinate point (y,z), and the angle of desired rotation in degrees can be read and recorded from the goniometer (goniometer is hidden in the drawing) attached to the planar rod holder and rod guide. From FIG. 3(b), the angle of rotation is in the x-y plane. Lastly, the amount of distraction is simply recorded from the graduated planar rod at the point relative to the planar rod guide.

FIG. 3 shows two different configurations for tenting a breast in the breast bracket. FIG. 3(a) shows a tented breast using a pentarod (5 rod) tenting scheme. FIG. 3(b) shows a tented breast using a quadrarod (4 rod) design scheme. Tenting of the breast in the breast bracket is not limited by these design schemes and in fact there exists a variety of breast tenting configurations that can be used to frame a breast in the breast bracket.

From FIGS. 2 and 3, there are 5 functional surfaces on the breast bracket, namely the anterior plane, medial plane, lateral plane, superior plane, and inferior plane. Because of symmetry of the breast bracket, the frames and components are interchangeable. Additionally, the geometry of the breast bracket can take a variety of geometric configurations including but not limited to square, rectangular, round, and oval to name a few.

FIG. 4 illustrates the biomechanical effects of framing the breast in the breast bracket. FIGS. 4(a) and 4(b) show the azimuthal rod-adhesive cup assembly adhered to the nipple-areola complex and distending the breast in the generally the anterior or z direction. The planar rod-adhesive cup assemblies are adhered to the skin of the breast but are in a relaxed position wherein no distraction of the breast has been invoked. FIGS. 4(c) and 4(d) show a breast in the distracted position causing the breast to distend in a direction parallel to the distracted rod. The displacement or distraction of the planar rods in opposite directions as shown in FIGS. 4(c) and 4(d) results in distension of the breast tissue along the x axis. In other words, displacement of the planar rods in the direction shown in FIGS. 4(c) and 4(d) cause an increase in the diameter of the breast along the x axis (increase in diameter from a to a') concomitant with shortening of the breast diameter generally along the y axis (decrease in diameter of the breast along the y axis).

Suppose now, the position of the displaced planar rods in 4(c) were held fixed and two new additional opposed planar rods were fixed to the skin of the breast such that the new rods were rotated 90 in the same plane as the original rods shown in FIG. 4(b). With the original planar rods held fixed, the new planar rods were equally and oppositely displaced along the y axis which would increase the diameter of the breast tissue along the y axis. The combined displacement of the original and new rods expands or tents the breast. Generally, however, the breast is considered to be tented and the tissue of the breast is stretched when any rod (planar or azimuthal) distracted causing the breast to be stretched. Furthermore, the breast bracket provide a method and device to position the breast in many desired positions in the breast bracket.

Figure 5:
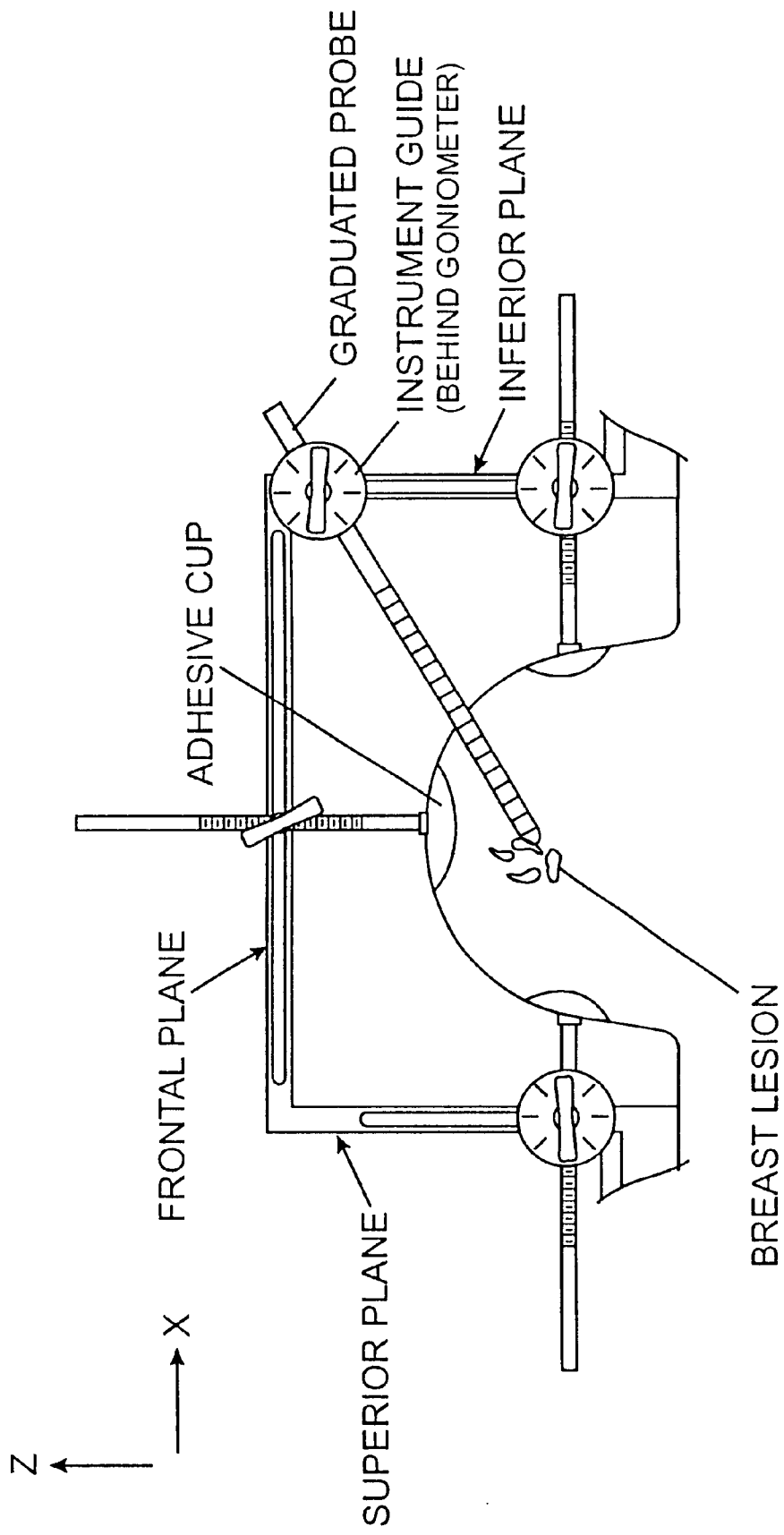
FIG. 5 is a side view of the breast framed in the breast bracket and the tip of a probe in a breast lesion. The precise location of the breast lesion can be determined from the graduated reference frame provided by the breast bracket.

After tenting of the breast is complete, a variety of procedures can be performed. The breast bracket can accommodate and facilitate a variety of procedures invoking a variety of instruments, devices, and techniques. In FIG. 5, a graduated probe is shown within the boundaries of a lesion. The position of the probe tip can be recorded and/or calculated. In this embodiment, the position of the final position of the probe in the x,y,z coordinate frame provided by the breast bracket by recording the (y,z) position of the instrument guide in the inferior plane, the position of the probe relative to the instrument guide, and the angle of the probe in the x-z plane. Recording and/or calculating the position of the probe allows the surgeon to locate the spatial position of the breast lesion relative to the graduated reference frame of the breast bracket. This would allow the surgeon to plan his surgery. If, for example, he would like to remove a spherical tissue specimen with a radius of 2.5 cm taken from the tip of the probe, then he would simply calculate the boundary of such a tissue sphere. Accordingly, the surgeon could limit his dissection to the surface of the sphere and outwardly.

In another embodiment depicted in FIG. 5, the Vitter and Lee device described in U.S. Pat. No. 6,022,362 could be fastened to the breast bracket in place of the probe. The tubular member of the Vitter and Lee device could be placed into the breast using the instrument guide attached to the inferior plane of the bracket. Additional stabilization, improved dexterity, and enhanced operation is achieved when the Vitter and Lee device is integrated into the breast bracket. For example, rotation of the bowed cutting edge in an effort the excise breast tissue is more efficient and performed in a more precise and controlled manner when the Vitter and Lee device is integrated into the breast bracket.

There are other devices and computer programs that would allow the aforementioned procedure to become much less cumbersome, thus simplifying the operative procedure while increasing the accuracy and consistency of such procedures. Take, for example, computer controlled surgical robots manufacture and sold by Computer Motion, Inc. (Santa Barbara, Calif.). These computer controller robots could be aligned to the reference frame of the breast bracket and make dissecting and removing a sphere of tissue as simple as inputting the (x,y,z) coordinate of the breast lesion and the radius of the breast tissue specimen to be dissected and removed. The breast bracket would allow the robot to function precisely within the reference frame facilitated by the breast bracket. In another embodiment, instruments used with the breast bracket frame are electronically monitored such that the position of a point on the instrument is always known with the breast bracket frame. Electronically monitoring included video triangulation and electronic triangulation.

Figure 6:
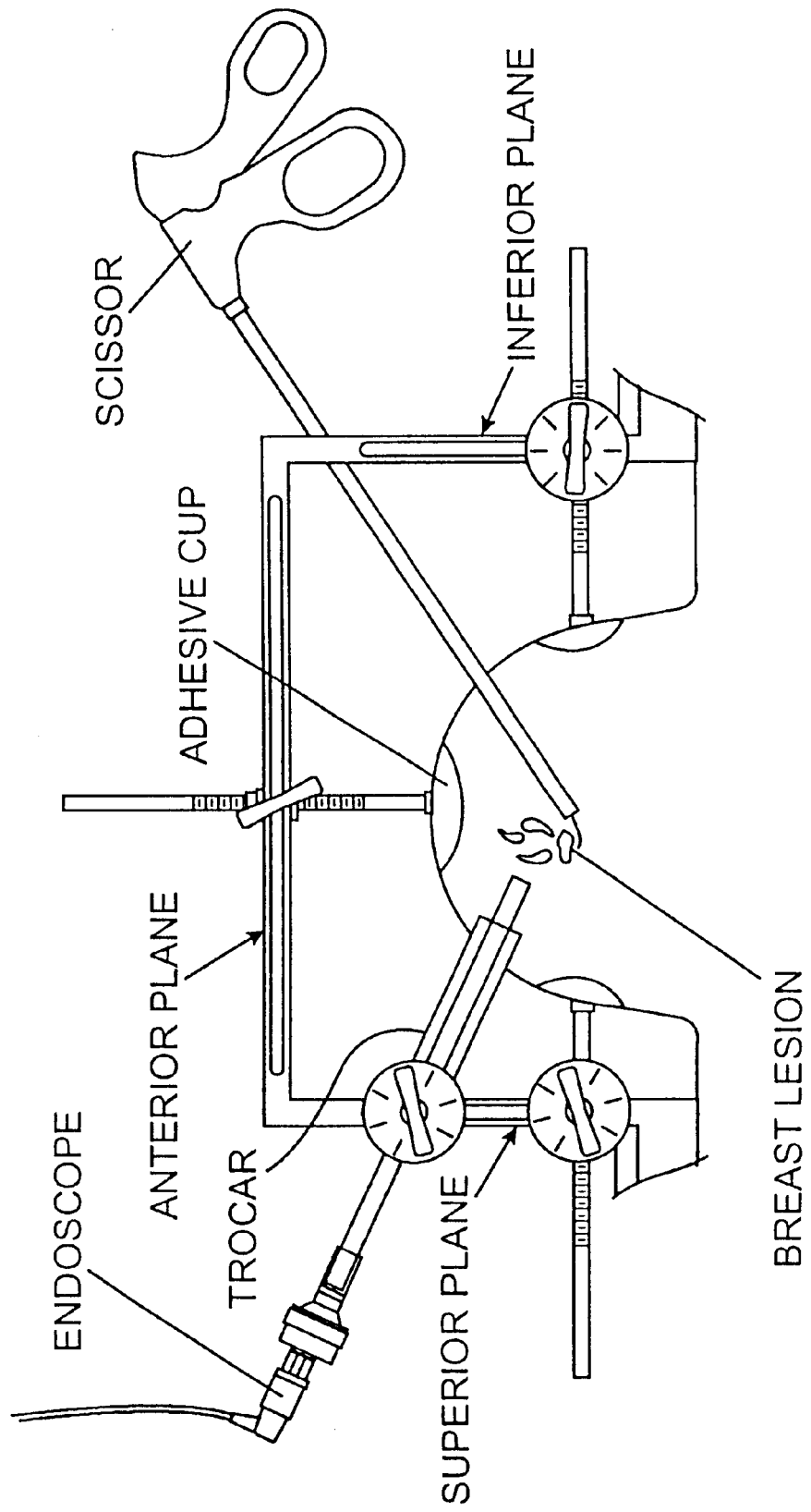
FIG. 6 is a side view of a breast framed in the breast bracket and undergoing mammoscopy.

The breast bracket can also facilitate mammoscopy as shown in FIG. 6. After the breast is tented, a stab incision is made with a scalpel and the trocar is threaded into the incision and fixed to the frame in the desired position on the superior plane. An endoscope with a working channel is passed in the lumen of the trocar. The endoscope allows visualization of the breast tissue while providing a working channel for instrumentation. In FIG. 6, opposite the endoscope, a scissor is shown reversibly and moveably attached on the inferior plane of the breast bracket. In another embodiment, an endoscope coupled to a camera that is sensitive to electromagnetic radiation in the mid-infrared range can be used to image the breast tissue.

The scissor-endoscope combination shown in FIG. 6 are one of the many instrument combinations used in laparoscopic procedures of the abdomen. The primary difference between laparoscopic procedures of the abdomen and mammoscopic procedures of the breast shown in FIG. 6 center on the methods and devices to tent or expand the abdomen and breast, respectively. In abdominal laparoscopic procedures, a Veress needle is introduced above the naval and into the abdominal free space. Carbon dioxide gas is pumped into the abdominal free space and the abdominal wall is distended, thus creating a significant volume of working space which is filled with gas. Trocars that are reasonably sealed and air tight are introduced through the abdominal wall after insufflation. An endoscope coupled to a camera is inserted through at least one of the trocars which allows visualization of the abdominal contents on a video monitor in the operating room. Thus, the positive gas pressure exerts a uniform outwardly directed force from inside the abdomen to outside the abdomen such that it causes the wall of the abdomen to expand.

Referring again to FIG. 6, unlike the abdominal cavity, the breast does not have any anatomic free space. In order to create working space, the breast should be uniformly distended or tented as shown in FIGS. 1 through 6. Incisions are made and dissection of the breast tissue proceeds and working space is created. The tented dome configuration of the breast is maintained throughout mammoscopic procedures of the breast since the fixed planar and azimuthal rods support fix the skin at specific points within the confines of the breast bracket. In addition, tenting of the breast distends the breast tissue, thus making dissection of breast much easier. Furthermore, distension of the breast in the breast bracket allows better visualization and repeatability since the breast is fixed in a graduated reference frame and stabilized. Visualization of the breast tissue is either direct with unaided or eye or through the use of an endoscope coupled to a camera that is sensitive to ultraviolet, visible, near-infrared, and/or mid-infrared light.

Figure 7A:
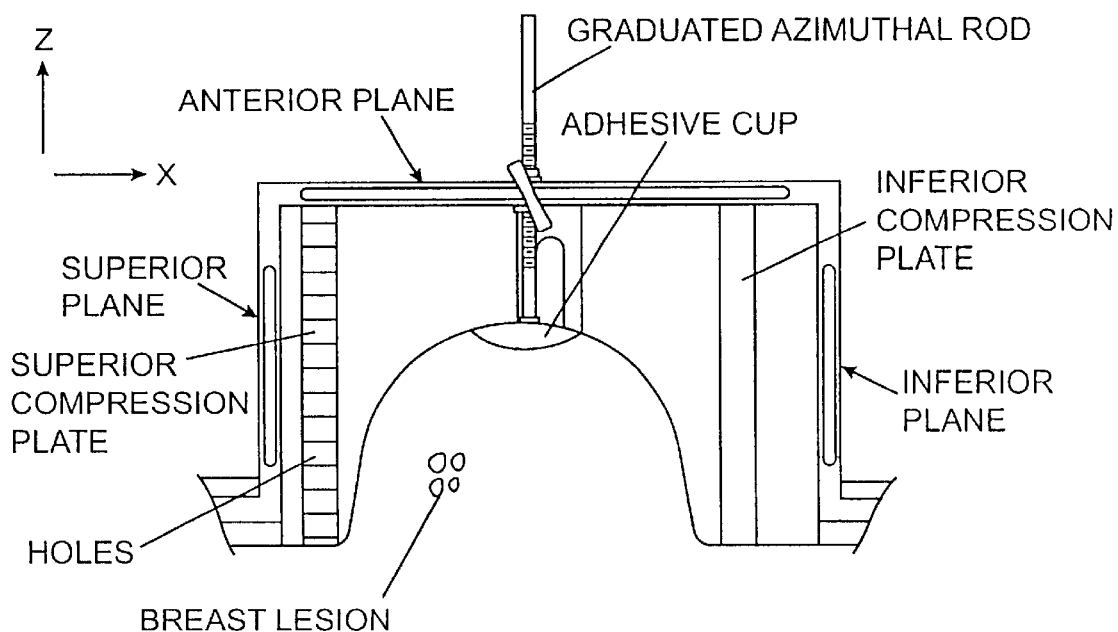
FIG. 7(a) shows a side view of the breast in the neutral position with the azimuthal rod distracting the breast in the anterior or z direction.
Figure 7B:
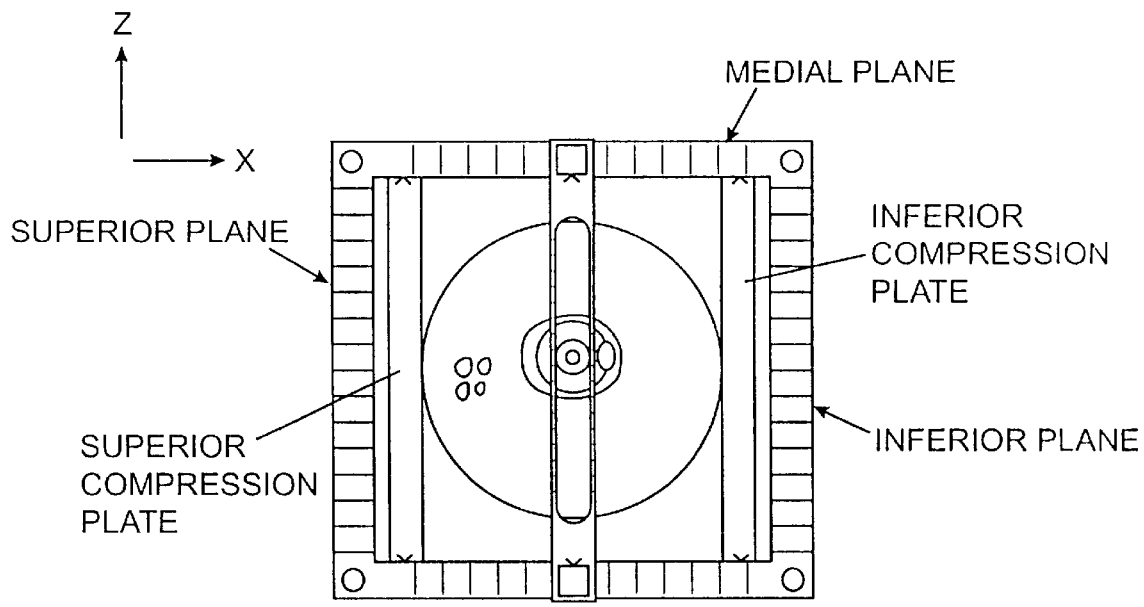
FIG. 7(b) shows a top view of the breast in the neutral position. Superior and inferior compression plates are reversibly and moveable attached to the breast bracket.
Figure 8A:
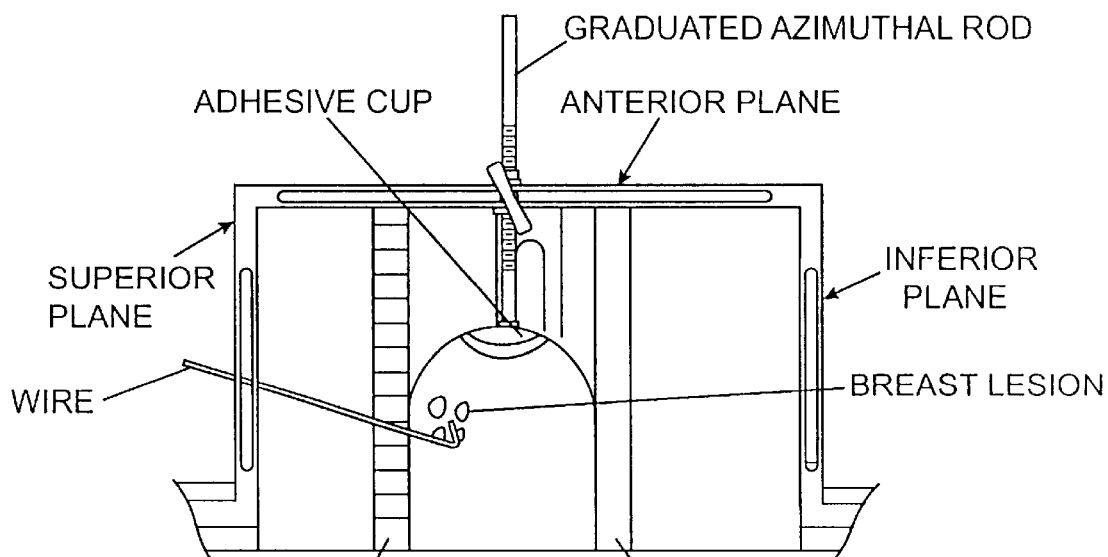
FIG. 8(a) shows a side view of the breast in the compressed position with a wire placed in or about a breast lesion under radiographic guidance.
Figure 8B:
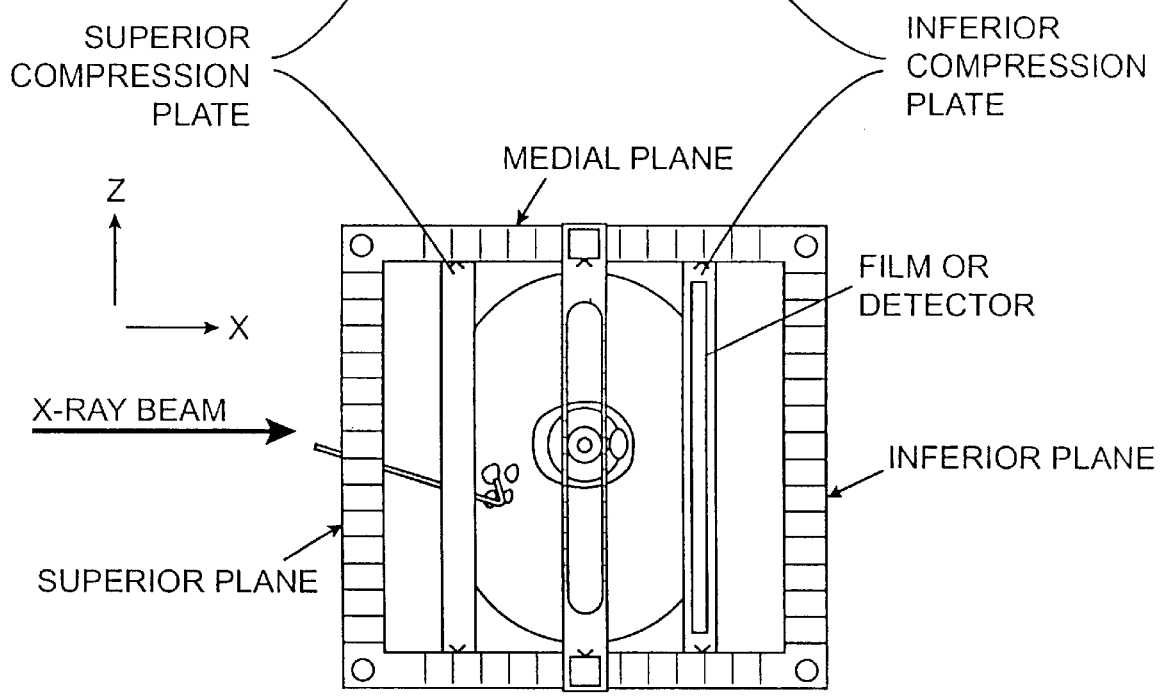
FIG. 8(b) show a top view of the breast in the compressed breast with a wire placed the breast tissue at the site of a breast lesion under radiographic guidance.

The breast bracket provides for radiography of the breast while the patient is on the operating table in the supine position. FIGS. 7 and 8 show a breast framed in the breast bracket in the neutral and compressed position for the purposes of radiography and radiographic guidance techniques such as the placement of a wire for wire needle location of breast lesions. The superior and inferior compression plates in FIGS. 7 and 8 are reversibly and moveable attached to the breast bracket.

FIG. 7 shows side and top views of the breast framed in the bracket in the neutral position with the azimuthal rod distracting the breast in the anterior or in the z direction. Also, in FIGS. 7 and 8, two compression plates with holes can be used to facilitate the use of devices and methods such as those describe in U.S. Pat. Nos. 5,795,308; 5,807,276; and 6,080,114.

FIG. 8 shows side and top views of the breast framed in the bracket in the compressed position. The superior and inferior compression plates are reversibly and moveable attached to the breast bracket and have been displaced toward one another so as to compress the breast along the axis of radiation.

FIG. 8 shows top views of a breast framed in the breast bracket undergoing radiography. The moveable superior and inferior compression plates are displaced toward one another along the x axis causing compression of the breast. FIG. 8($a$) shows a side view of the breast in the compressed position with a wire placed proximate to a breast lesion under radiographic guidance. FIG. 8($b$) show a top view of the breast in the compressed position with a wire placed through a hole in the compression plate and into the breast tissue and proximate to the breast lesion under radiographic guidance. The wire can be graduated. Thus, once the wire is placed and the compression plates removed and the breast framed in the breast bracket, the proximal end of the stiff wire can be positioned and fixed to the breast bracket. At this point, the location of the breast lesion within the breast bracket can be calculated by recording the coordinates of the proximal end of the wire, length of the wire from the breast bracket to the distal aspect of the wire, and the direction of the wire from the breast bracket to the breast lesion.

In clinical situations wherein a second procedure on a breast is required in a breast that has been framed in the breast bracket, the breast bracket can aid the surgeon in recreating the position of the breast as it was in the first procedure or reference procedure. In other words, the breast can be repeatedly brought into the same position or reference position by simply framing the breast in the same manner as in the reference procedure. To bring the breast back to the reference position requires at reference points that are relative to the patient's body and the operating table. The suprasternal-naval gauge shown in FIGS. 9 and 10 offers one method and device that facilitates repeatable placement of the breast in the breast bracket.

Referring to FIG. 9($a$), it shows a top view of anterior aspect of the graduated suprasternal-naval gauge reversibly placed in the suprasternal notch and the sliding naval index placed in the naval. After placement of the suprasternal and naval indexes in the suprasternal notch and naval, respectively, the distance from the naval to the suprasternal notch can be read and record at the level of the naval. FIG. 9($b$) shows side view of the graduated suprasternal-naval gauge showing the hemispherical suprasternal and naval indexes.

Figure 10:
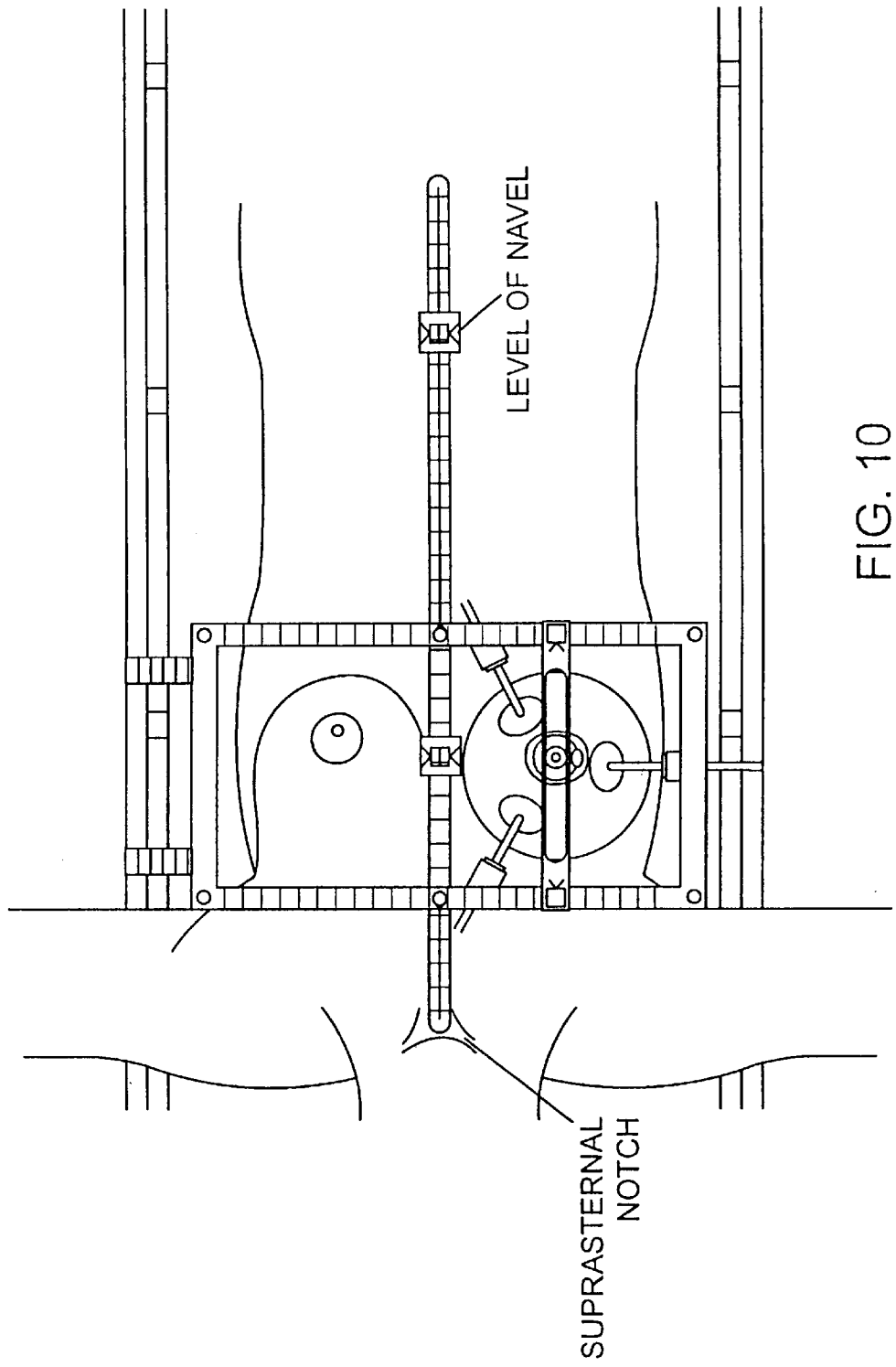
FIG. 10 is a top view of the graduated suprasternal-naval gauge reversibly coupled to the breast bracket. The gradu-ated suprasternal-naval gauge allows the breast to be repeatedly framed in the breast bracket at the same position.

Once the suprasternal-naval gauge is positioned on the patient, the breast bracket is assembled and integrated with the suprasternal-naval gauge. FIG. 10 shows the suprasternal-naval gauge and the relative position of the breast bracket to the suprasternal-naval gauge and the operating table. Therefore, for repeatability, the position of the breast bracket to the suprasternal-naval gauge and the operating are recorded. The last step calls for the framing of the breast in the desired position and recording all positions of rods relative to the breast bracket.

Although, the aforementioned description of the method and devices for the breast bracket describe a graduated reference, there are clinical situations wherein a graduate breast bracket is not required or necessary. Thus, a breast bracket without graduations can be used.

The breast bracket also functions as a stabilized retractor.

What is claimed is:

1. A method stabilizing a breast during surgery, said method comprising:
   positioning the breast within a reference frame under conditions such that the breast may be repeatedly positioned within the frame for subsequent procedures;
   identifying an external surface of the breast; and
   tensioning the surface outwardly to maintain the tissue structure in a defined configuration, wherein tensioning is performed relative to the reference frame so that the breast can be repeatedly positioned within the brace for subsequent procedures.

2. A method as in claim 1, wherein tensioning comprises:
   securing a plurality of stabilizing elements in the bracket positioned over the patient, engaging ends of the stabilizing elements into or onto the breast, and adjusting the positions of the stabilizing elements in the frame to evenly and repeatably tension the tissue structure.

3. A method as in claim 1, wherein the reference frame is graduated and tensioning of the breast surface relative to the graduations is noted so that the breast may be repeatably positioned in a subsequent procedure.

4. A method for stabilizing a breast during surgery, said method comprising:

positioning the breast within a reference frame;

attaching a plurality of stabilizing elements to an external surface of the breast, wherein the stabilizing elements are adjustably attached to the reference frame; and tensioning the stabilizing elements outwardly from the surface to maintain the breast in a defined configuration.

5. A method as in claim 4, wherein the stabilizing elements are positioned relative to graduations on the frame so that the positions of the stabilizing elements may be repeated in a subsequent procedure.

6. A method as in claims 1 or 4, wherein positioning the breast comprises aligning the frame with at least one of the navel and the suprasternal notch.

7. A tissue stabilization bracket system comprising:

a bracket that can be mounted over a patient, wherein the patient is immobilized relative to the bracket;

means for repeatably positioning the bracket relative to at least one of the patient's navel and suprasternal notch; and a plurality of stabilizing elements adjustably mountable on the bracket and having engagement portions that can secure and tension a tissue surface of a tissue structure.

8. A tissue stabilization bracket system as in claim 7, wherein the bracket includes a plurality of or rod guides located in the superior, inferior, medial, and lateral planes.

9. A tissue stabilization bracket system as in claim 8, wherein the stabilizing elements comprise rods adjustably mounted in the rod guides.

10. A tissue stabilization bracket system as in claim 9, wherein the engagement portions comprise adhesive pads.

11. A tissue stabilization bracketed system as in claim 9, where at least one rod is arranged along an azimuthal line to engage in the nipple-areola complex from above.

\* \* \* \* \*